United States Patent
O'Brien et al.

(10) Patent No.: US 11,856,924 B2
(45) Date of Patent: Jan. 2, 2024

(54) GARMENT

(71) Applicant: AQUILA EQUINE LIMITED, Piltown (IE)

(72) Inventors: Anne Marie O'Brien, Cashel (IE); Thomas Anthony Curtis, Enniscorthy (IE)

(73) Assignee: Equimetrics Limited, Piltown (IE)

( * ) Notice: Subject to any disclaimer, the term of this patent is extended or adjusted under 35 U.S.C. 154(b) by 847 days.

(21) Appl. No.: 16/308,911

(22) PCT Filed: Jun. 12, 2017

(86) PCT No.: PCT/IE2017/000010
§ 371 (c)(1),
(2) Date: Dec. 11, 2018

(87) PCT Pub. No.: WO2017/216783
PCT Pub. Date: Dec. 21, 2017

(65) Prior Publication Data
US 2019/0150406 A1     May 23, 2019

(30) Foreign Application Priority Data
Jun. 13, 2016   (IE) .................................... 2016/0161

(51) Int. Cl.
*A01K 29/00*     (2006.01)
*A01K 13/00*     (2006.01)
(Continued)

(52) U.S. Cl.
CPC .......... *A01K 29/005* (2013.01); *A01K 11/008* (2013.01); *A01K 13/008* (2013.01);
(Continued)

(58) Field of Classification Search
CPC ... A01K 29/005; A01K 11/008; A61B 5/6801
(Continued)

(56) References Cited

U.S. PATENT DOCUMENTS

| 6,615,568 B1 * | 9/2003 | Roskies | .................... B68C 1/12 54/66 |
| 7,683,883 B2 * | 3/2010 | Touma | .................... G06F 3/017 345/157 |

(Continued)

FOREIGN PATENT DOCUMENTS

| GB | 2465640 A | 6/2010 |
| WO | 2004084624 A1 | 10/2004 |

OTHER PUBLICATIONS

The Irish Field: Horse Sense: There's an app for that. Feb. 12, 2016. www.theirishfield.ie/horse-sense-theres-an-app-for-that-200052/, 3 pages.

(Continued)

*Primary Examiner* — Richard T Price, Jr.
(74) *Attorney, Agent, or Firm* — RatnerPrestia

(57) ABSTRACT

A smart animal garment 1, such as a horse blanket 1, for an animal 5 in which the garment 1 can extend around the chest area 8*a*, shoulders 27 and towards the hindquarters of the animal 5 and is fitted with sensors 3 for monitoring the health and wellbeing of the animal 5 and the data parameters detected by the sensors 3 are communicable to a stable mounted communications hub 6 via a monitor 4 located for example at the chest portion 8*a* of the garment 1.

18 Claims, 16 Drawing Sheets

(51) Int. Cl.
    *A61B 5/00*     (2006.01)
    *A01K 11/00*     (2006.01)
    *A61B 5/0205*     (2006.01)
    *A61B 5/0533*     (2021.01)
    *A61B 5/11*     (2006.01)
    *B68C 1/02*     (2006.01)
    *B68C 1/12*     (2006.01)
    *A61B 5/024*     (2006.01)
    *A61B 5/08*     (2006.01)

(52) U.S. Cl.
    CPC .......... *A61B 5/002* (2013.01); *A61B 5/02055* (2013.01); *A61B 5/0533* (2013.01); *A61B 5/11* (2013.01); *A61B 5/1112* (2013.01); *A61B 5/6801* (2013.01); *A61B 5/6804* (2013.01); *A61B 5/6805* (2013.01); *B68C 1/02* (2013.01); *B68C 1/12* (2013.01); *A61B 5/024* (2013.01); *A61B 5/0816* (2013.01); *A61B 2503/40* (2013.01); *A61B 2562/0219* (2013.01)

(58) Field of Classification Search
    USPC ................................................ 119/850, 174
    See application file for complete search history.

(56) References Cited

U.S. PATENT DOCUMENTS

| | | | | |
|---|---|---|---|---|
| 8,325,138 | B2* | 12/2012 | Touma | G06F 3/017 345/157 |
| 8,364,257 | B2* | 1/2013 | Van Den Eerenbeemd | A61B 5/6843 607/2 |
| 9,266,233 | B2* | 2/2016 | Kornbluh | B25J 9/0006 |
| 9,317,108 | B2* | 4/2016 | Touma | G06F 3/014 |
| 9,900,669 | B2* | 2/2018 | Touma | H04Q 9/00 |
| 9,999,392 | B1* | 6/2018 | Wordham | A61B 5/0245 |
| 2008/0236500 | A1* | 10/2008 | Hodges | A61B 5/036 119/14.02 |
| 2010/0036277 | A1* | 2/2010 | Austin | A61D 13/00 600/549 |
| 2013/0217980 | A1* | 8/2013 | Elser | A01K 29/005 600/301 |
| 2014/0338447 | A1* | 11/2014 | Sharpe | A01K 11/00 73/431 |
| 2015/0015192 | A1* | 1/2015 | Leabman | A01K 11/008 320/108 |
| 2015/0157435 | A1 | 6/2015 | Chasins et al. | |
| 2017/0100300 | A1* | 4/2017 | Rapp | A61F 13/06 |
| 2018/0139929 | A1* | 5/2018 | Hill | A01K 13/006 |
| 2020/0060545 | A1* | 2/2020 | Maher | A61B 5/0022 |
| 2020/0113728 | A1* | 4/2020 | Spector | A61B 5/6805 |
| 2020/0134272 | A1* | 4/2020 | Ruiter | H01Q 21/28 |
| 2021/0000195 | A1* | 1/2021 | Temeng | A41D 27/28 |
| 2021/0022676 | A1* | 1/2021 | Lamego | G08C 15/06 |
| 2021/0045686 | A1* | 2/2021 | Wiese | A61B 5/6804 |

OTHER PUBLICATIONS

International Search Report issued in PCT/IE2017/000010, dated Aug. 17, 2017, 4 pages.
Written Opinion of the International Searching Authority issued in PCT/IE2017/000010, dated Aug. 17, 2017, 5 pages.

* cited by examiner

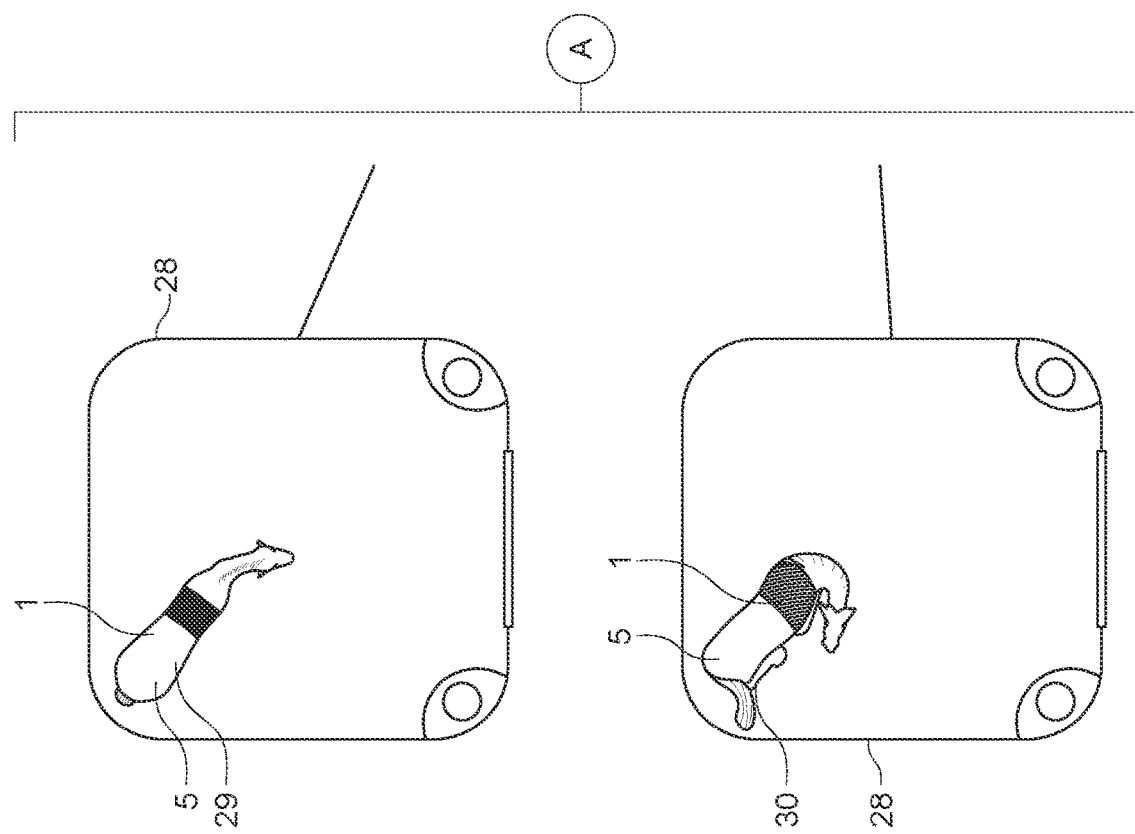

GARMENT

CROSS REFERENCE TO RELATED APPLICATIONS

This application is the U.S. National Phase Application of PCT/IE2017/000010, filed Jun. 12, 2017, which claims priority to Ireland Patent Applicant No. 52016/0161, filed Jun. 13, 2016, the contents of such applications being incorporated by reference herein.

Introduction

This invention relates to a smart animal garment and more particularly to a smart non-human animal garment or blanket for monitoring and enhancing the health, wellbeing, performance and recovery of an animal. The invention also relates to a monitoring system comprising the smart animal garment.

BACKGROUND OF THE INVENTION

The health and wellbeing of non-human animals is largely dependent on the subjective ability of veterinarians, owners, trainers and the like to observe and interpret the behaviour of the animals. For example, a range of factors can act as indicators as to the wellbeing and performance of an animal such as high performance thoroughbred racehorses and showjumpers. A small change in an indicating factor such as a horse's heartrate or temperature can be indicative of a potentially serious underlying problem such that early identification of the change in the indicating factor can be critical to the prevention of injury to, or serious illness in, the horse. However, as it is not possible for animals such as horses to directly communicate physiological changes to veterinarians, owners and trainers, frequently, such symptomatic changes in indicating factors may only become observable long after onset of the change in the indicating factor with the result that treatment or prevention of injury to the horse is delayed. Moreover, even where a symptomatic change is observed, the animal must be subjected to an examination with multiple medical devices such as thermometers and heartrate monitors to diagnose changes in temperature and heartrate.

Various devices are known for monitoring a horse's health, wellbeing and performance. For example, SeeHorse (Trade Mark) and Nightwatch (Trade Mark) monitoring devices are known for use with horses to monitor various parameters such as temperature. However, both the SeeHorse (Trade Mark) and the Nightwatch (Trade Mark) devices must be supported on a collar, halter or strap secured to the horse's head or neck region. Clearly, this is undesirable when the horse is unattended as head collars, halters or straps can result in injury to an animal e.g. by becoming caught on feeders and the like in stables. This is particularly problematic where high value horses such as racehorses are to be monitored with the result that such devices are not widely employed. Moreover, parameter measurements such as temperature taken at a horse's neck or head are known to be subject to inaccuracies while it is also difficult to accurately monitor a horse's movement or gait via a head-mounted monitoring device.

SUMMARY OF THE INVENTION

According to an aspect of the invention an animal garment for monitoring the animal comprising at least one sensor on the garment communicable with a user.

Advantageously, the garment comprises a plurality of sensors.

Preferably, the garment is mountable on the animal trunk or torso. More preferably, the garment comprises a back portion, a side portion depending from the back portion and a chest portion.

Suitably, the sensors are selected from the group comprising movement sensors, temperature sensors, pressure sensors, moisture sensors, respiration sensors, sound sensors, security sensors, heart monitor sensors, global positioning system (GPS) sensors and cameras. Preferably, the sensors comprise movement, temperature and respiration sensors.

Advantageously, the movement sensors comprise inertia sensors. Preferably, the inertia sensors are selected from the group comprising accelerometers, magnetometers and gyroscopes.

Suitably, the moisture sensors comprise galvanic skin response electrodes.

Preferably, the temperature sensors comprise IR and/or thermocouple temperature sensors.

Advantageously, the respiration sensors comprise variable impedance fabric sensors.

Optionally, the sensors are located in a sensor zone on the garment.

Preferably, the garment further comprises a monitor communicable between the sensors and an external communications hub. More preferably, the external communications hub is locatable adjacent the garment.

In a preferred embodiment of the invention, the garment comprises a horse garment.

Preferably, the horse garment comprises a horse blanket. More preferably, the horse blanket is selected from the group comprising full blankets, half blankets, horse rugs, stable blankets, night blankets, turn-out rugs, rain sheets, coolers, anti-sweat sheets, fly sheets, therapeutic blankets, under rugs, half-sheets, half blankets, quarter sheets, saddle cloths, girth sleeves and rump rugs.

Alternatively, the horse garment comprises a horse vest, a saddle pad or a saddle.

An aspect of the invention also extends to a system for monitoring the wellbeing, performance or recovery of an animal comprising the garment as hereinbefore defined and an external communications hub. Preferably, the external communications hub is locatable adjacent the garment. Alternatively, the external communications hub comprises a cloud based communications hub communicable with the garment.

Preferably, the system further comprises at least one environmental sensor for detecting ambient conditions adjacent the garment.

More preferably, the at least one environmental sensor is located at the communications hub. Most preferably, the system comprises a plurality of environmental sensors.

Suitably, the environmental sensors are selected from the group comprising air quality sensors, ambient light sensors, thermometers and cameras.

Preferably, the system further comprises an analytics module communicable with the communications hub for analysing data from the sensors.

Preferably, the system further comprises an alert/flag system for generating alerts/flags for a user. More preferably, the alerts/flags are communicable to a user via a mobile or web based user interface.

In a preferred embodiment of the invention the system comprises a system for monitoring the wellbeing of a horse.

The advantages of the invention are many. The garment and system of aspects of the invention provide accurate and verifiable information on the health and wellbeing of animals. When used with animals such as horses, the smart garment mounted sensors provide reliable data on the condition of the horse while the environmental sensors provide accurate information on ambient conditions which can be compared with the data provided by the garment mounted sensors to determine the impact, if any, of ambient conditions on the wellbeing of the horse. As the garment of the invention can conform in shape and configuration to the anatomy of the horse, the data harvested from the sensors of the smart garment is reliable and accurate.

The garment of an aspect of the invention is suitable for use with all types of sensors such as movement sensors, temperature sensors, pressure sensors, moisture sensors, respiration sensors, sound sensors, security sensors, heart monitor sensors, GPS sensors, cameras and any other sensor that can be used, for example, to monitor the health, wellbeing, security, performance and recovery of an animal. Unlike sensors mounted at the head or neck of a horse, the garment mounted sensors are located at the horse's trunk or torso between the neck and tail to provide accurate information and are not susceptible to external interferences while sensors can be positioned as required on the garment close to desired anatomical features e.g. heart rate sensors can be located on girth sleeves close to a horse's heart.

The system of an aspect of the invention is adapted to flag potential problems when detected measurements deviate from the norm and allows for the retrieval of reliable, relevant measurements twenty-four hours a day which can be interpreted in an appropriate fashion. As the sensors are effectively body-mounted via the smart garment, movement anomalies which can give the erroneous readings associated with head or neck mounted sensors are eliminated. This is of particular utility with smart horse blankets and the like.

The system of an aspect of the invention can exploit data harvested from the sensors to validate known health predictors and 'learn' each horse's normal behaviour patterns to better predict potential problems and eliminate false positives.

The garment and system of aspects of the invention can also serve as an early warning system during foaling and other reproductive applications and can also be used to monitor colic, orthopaedic casts and recovery and a multitude of other diseases and injuries.

The garment and system of aspects of the invention can also serve as an invaluable training aid and can also be used in animal performance analysis and to analyse animal recovery rates and the like where the garment of the invention is worn by an animal before, during and/or after exercise, competition and the like.

The blanket and system of aspects of the invention can also function effectively as a security device and system to alert owners if an animal is being moved without authorisation or being tampered with.

BRIEF DESCRIPTION OF THE DRAWINGS

Aspects of the invention will now be described by way of example only with reference to the accompanying drawings and Example in which:

FIG. 9(a) is a schematic view from above of a horse in its stable wearing the horse vest of FIG. 4 fitted with a barometric pressure sensor with the horse, firstly, in a standing position and, secondly, in a lying position;

DETAILED DESCRIPTION OF THE DRAWINGS

Figure 1:
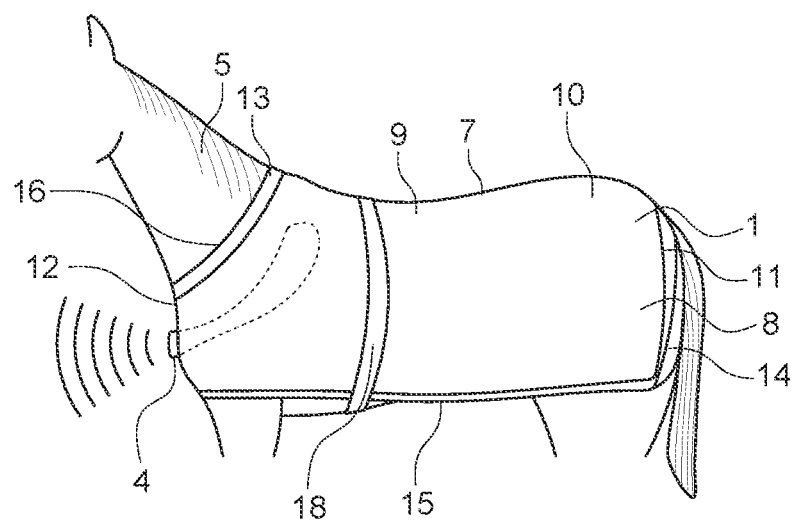
FIG. 1 is a perspective view from one side of a first embodiment of a smart horse garment of the invention in form of a smart blanket fitted and conforming to a horse in which the horse blanket is a full horse blanket extending around the chest area, shoulders and towards the hindquarters of the horse which is fitted with sensors for monitoring the health and wellbeing of the horse and the data parameters detected by the sensors are communicable to a stable mounted communications hub via a monitor located at the chest area of the horse on the horse blanket.

As shown in the drawings a smart garment for monitoring the health and wellbeing of an animal is generally indicated by the reference numeral 1. For the purposes of the following description the smart garment 1 is described as a smart horse blanket 1. However, as will be appreciated by those skilled in the art, the smart blanket 1 can be used with any suitable animal ranging from animals kept in a zoo and the like to humans although the smart blanket 1 does have particular application in the equine industry due to the high value of thoroughbreds. Moreover, the term "garment" embraces blankets, vests or other garments and garment-type articles that can be worn by an animal including saddles and saddle pads while the horse blanket of the invention can include full blankets, half blankets, horse rugs, stable blankets, night blankets, turn-out rugs, rain sheets, coolers, anti-sweat sheets, fly sheets, therapeutic blankets, under rugs, half-sheets, half blankets, quarter sheets, rump rugs, saddle pads, saddle cloths, girth sleeves and the like.

Generally, the smart horse blanket 1 can have a sensor zone 2 fitted with horse sensors 3 for remotely monitoring horse health, wellbeing, performance and recovery. As shall be explained more fully below, examples of suitable sensors include, inter alia, heart rate sensors, respiratory sensors, movement sensors, temperature sensors, pressure sensors, moisture sensors, security sensors, GPS sensors, warning alarms and the like. However, the garment 1 of the invention is suitable for use with any type of sensor for monitoring the health, wellbeing, performance, recovery and the like of an animal. The sensors 3 can be located and secured or incorporated as required in the sensor zone 2 or, as described further below, at other locations on/in the garment 1 using suitable attachment means as necessary. The location of the sensors 3 can depend on the nature of the sensor and/or the type of garment, e.g. due to the location of a horse's heart, girth sleeves are particularly suitable for use with heart rate sensors positioned on the girth sleeve.

The sensors 3 are communicable with a monitor 4 on the horse blanket 1 for communicating data from the horse blanket 1 when placed on a horse 5 to a communications hub 6 mounted in the vicinity of the horse 5—e.g. a stable-mounted communications hub 6.

The horse blanket 1 has a back portion 7 extending between a neck end and a tail end of the horse blanket 1, two side portions 8 depending from the back portion 7 and a chest portion 8a contiguous with the side portions 8. In use on the horse 5, the back portion 7 extends along the back 9 of the horse 5 towards the hindquarters while the side portions 8 depend along the sides 10 of the horse 5 in conventional fashion. In the present embodiment, the side portions 8 extend between the tail end 11 of the horse 5 and the chest portion 8a at the chest area 12 of the horse 5.

Figure 2:
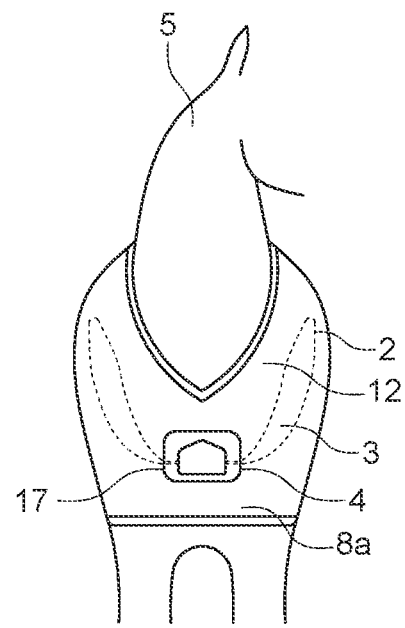
FIG. 2 is a front perspective view of the smart horse blanket of FIG. 1 with the sensor zone in which the sensors are mounted either side of the monitor indicated by broken lines.

The horse blanket 1 has a front edge 13, a rear edge 14 and two side edges 15. A contoured neck opening 16 is formed at the front edge 13 while a monitor mounting 17 is provided on the horse blanket 1 at the chest portion 8a for supporting the monitor 4. The horse blanket 1 is further provided with a closure strap or bellyband 18 at the side portions 8 to secure the blanket 1 in position on the horse 1. The horse blanket 1 can be sized as required. For example, as shown in FIGS. 1 and 2, the horse blanket 1 can extend fully along the back 9 of the horse 1 (a full horse blanket 1) or can be a half-blanket or vest 1 conforming to the anatomy or conformation of the horse as shown in FIG. 3 in which the half-blanket 1 is made up of a shortened back portion 7 which extends over the withers 26 of a horse 5 and the two side portions 8 depend from the back portion 7 over the shoulders 27 of the horse and form the chest portion 8a.

Figure 3:
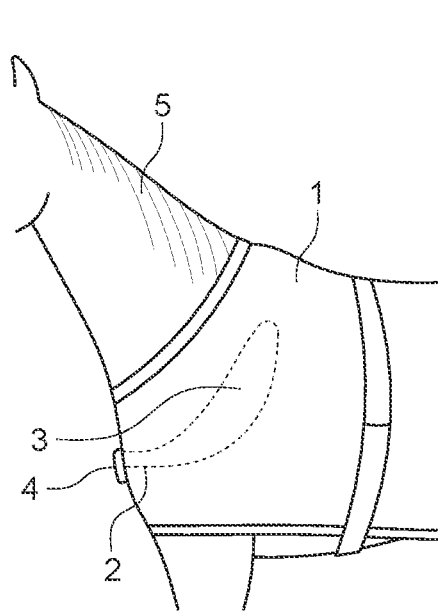
FIG. 3 is a side perspective view of a second embodiment of the smart horse blanket of the invention on a horse in which the horse blanket is a horse half blanket or vest conforming to the anatomy of the horse.
Figure 4:
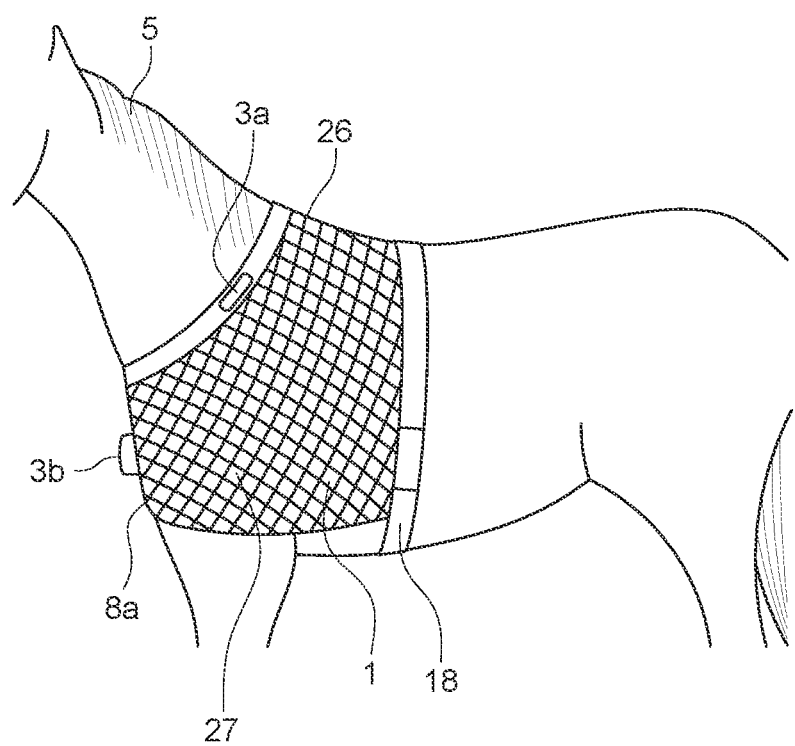
FIG. 4 is a side perspective view of a third embodiment of the smart horse blanket of the invention on a horse in which the horse blanket is a horse half blanket or vest as shown in FIG. 3 and the temperature sensors are mounted on the front edge of the horse blanket and the motion sensors are mounted at the chest area of the horse blanket.

FIG. 4 is a side perspective view of a third embodiment of the smart horse blanket 1 of the invention on a horse 5 in which the horse blanket 1 is a horse half blanket or vest 1 broadly similar to the half blanket shown in FIG. 3. However, in the present embodiment, a temperature sensor 3a is mounted on the front edge 13 of the vest 1 at the neck opening 16 and a motion sensor 3b is mounted on the vest 1 at the chest area 12 of the horse 5. The temperature sensors 3a can be located as required on the vest 1. However, by positioning the motion sensors 3b at the chest area 12 any impact of vest 1 movement over long periods on the motion sensors 3b was minimised.

Figure 5:
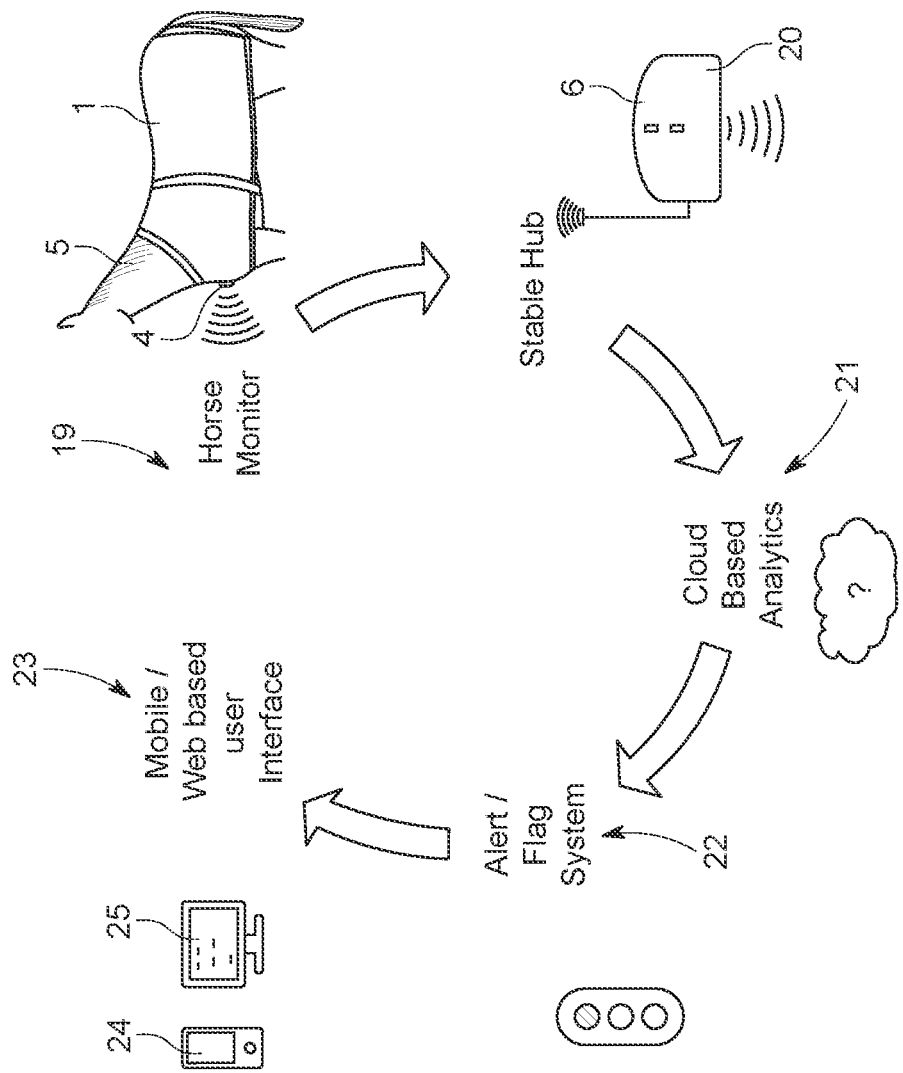
FIG. 5 is a schematic representation of an animal health and wellbeing monitoring system including the smart horse blanket of the invention and the stable communications hub which is in turn communicable with a cloud based analytics module and a mobile/web based user interface for transmitting alerts and data to a user.

FIG. 5 shows a schematic representation of an animal health and wellbeing monitoring system of the invention generally indicated by the reference numeral 19 which includes the smart horse blanket of FIGS. 1 to 4. As shown in the drawing, data on the health and wellbeing of the horse 5 detected by the sensors 3 in the sensor zone 2 is gathered at the monitor 4 on the horse blanket 1 and is communicated to the stable mounted communications hub 6. The stable mounted communications hub 6 can also include environmental sensors 20 for detecting and recording ambient environmental conditions in the vicinity of the horse 5 so that the impact of environmental conditions such as temperature, moisture and even air small particle levels on the parameters detected by the horse sensors 3 can be monitored and analysed.

The stable communications hub 6 is in turn communicable with a remote analytics module or server such as a cloud based analytics module 21 where the data harvested from the horse sensors 3 and environmental sensors 20 can be analysed algorithmically to assess and extract information on the health, wellbeing, performance, recovery and the like of the horse 5. The results and data of the analysis are then used to generate alerts/flags, updates, performance and recovery reports as required via an alert/flag system 22. The generated alerts/flags or updates can then be communicated to a user such as an owner/breeder or trainer via a mobile or web based user interface 23 as required. The user can receive the generated alerts/flags or updates on a handheld mobile device such as smartphone or tablet 24 or a personal computer 25 or the like.

The horse sensors 3 employed in the horse blanket 1 can be any suitable sensors 3 which can be located on the horse blanket 1 in a sensor zone 2 as described above in FIGS. 1 to 3 or elsewhere on the horse blanket 1 as required as shown in FIG. 4. However, it has been found that inertia sensors such as low gain accelerometers, magnetometers and gyroscopes are particularly suitable when used in the blanket 1 as a highly accurate indication of the horse's movement can be determined in contradistinction with movement sensors placed on the neck or head of a horse which result in highly unreliable movement data. Suitable moisture sensors include galvanic skin response electrodes while both IR and thermocouple temperature sensors are preferred. Variable impedance fabric sensors can be employed to monitor respiration while microphones can also be used to detect frequency analysis for other analyses. Bluetooth connectivity can also be used with the sensors 3.

The blanket 1 can also incorporate security sensors 3 to effectively act as a security device and system to alert owners if an animal is being moved without authorisation or being tampered with.

Suitable horse sensors 3 are available from Texas Instruments (Trade Mark), Shimmer (Trade Mark) and IBM (Trade Mark).

The environmental sensors 20 can be selected as required to monitor desired ambient conditions at the stable mounted communications hub 6. Examples of such sensors 20 include, but are not limited to, optical air quality sensors, ambient light sensors, thermometers and cameras. As indicated above, such environmental sensors 20 allow for the cross-referencing of the horse sensor 3 data and the ambient data to identify and explain horse behavior or changes in wellbeing e.g. if a horse suddenly becomes upset it may be because someone has switched on a stable light or a horse cough may be as a result of high ambient particulate or dust levels e.g. from fresh straw.

The horse sensors 3 and environmental sensors 20 facilitate the detection and analysis of multiple parameters such as changes in motion/bio signals warranting investigation e.g. raised respiration/heart rates, changes in eating/drinking behavior, difficulty in lying down/getting up, displays of discomfort such as excessive sweating, rolling or box walking.

The communications methods employed in the monitoring system can be any suitable system such as GSM, Wi-Fi, Low Power Wi-Fi, radio waves (e.g. 433 MHz), Bluetooth or combinations of the above.

The smart garment of the invention and in particular the horse blanket 1 can be manufactured from any suitable material although a lightweight, stretchable and breathable vest-type garment formed from Lycra or a similar material is preferred which could be employed indoors and outdoors in warmer climates. The horse blanket 1 can be sized as required but a tight-fitting garment is usually preferred in order to optimize sensor performance.

As indicated above, the smart garment 1 can be used to monitor the health, wellbeing, performance and recovery of an animal such as a horse 5 depending on how the garment 1 is employed. For example the smart horse garment 1 can be used on a horse when training or competing to extract and analyse data on the horse's performance, recovery rate and the like.

Example

The vest 1 of FIG. 4 in the form of a tight-fitting lightweight Lycra vest 1 fastened with a Velcro (Trade Mark) bellyband 18, was employed to monitor seventeen pregnant mares close to foaling as follows. The mares were monitored with the vest 1 of the invention for periods ranging from two to nine days and, in order to corroborate the data from the vest 1, the mares were also monitored using high resolution CCTV cameras throughout.

Figure 11:
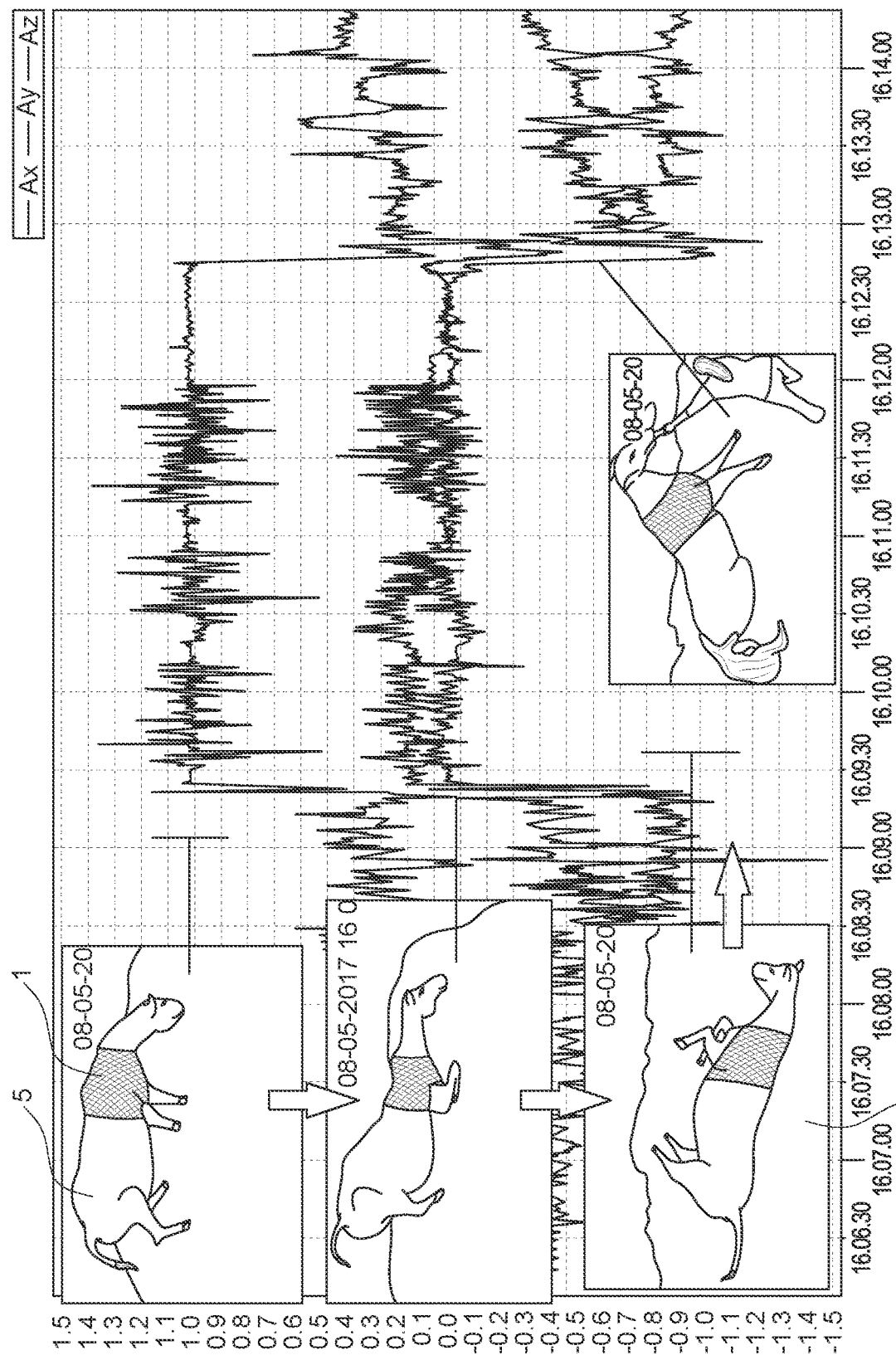
FIG. 11 is a combined graph and CCTV images of a mare fitted with the smart vest of FIG. 4 having a movement sensor in the form of an accelerometer with the mare in foal, with the CCTV images corroborating the accelerometer foaling data over a ten minute period.

The data from the sensors was synchronized with the video footage to corroborate the sensor data (see for example FIG. 11).

A variety of motion sensors 3b available from Shimmer (Trade Mark), Gulf Coast Data Products (Trade Mark) and Texas Instruments (Trade Mark) and temperature sensors 3a available from Omeron (Trade Mark) and Elitech (Trade Mark) were employed. Skin impedance sensors available from Shimmer (Trade Mark) were also incorporated into the smart vest 1. Multiple sensor arrays in various combinations were employed to assess the wellbeing of the subjects.

Figure 6A:
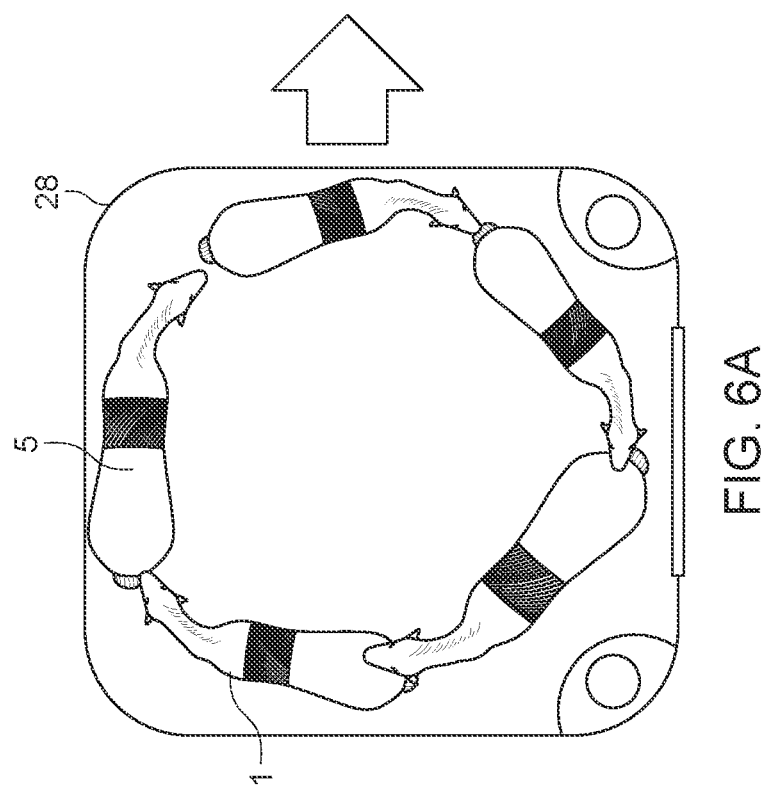
FIG. 6(a) is a schematic view from above of a horse in its stall or stable wearing the horse vest of FIG. 4 fitted with a motion sensor in the form of a magnetometer with the horse exhibiting box walking behaviour.
Figure 6B:
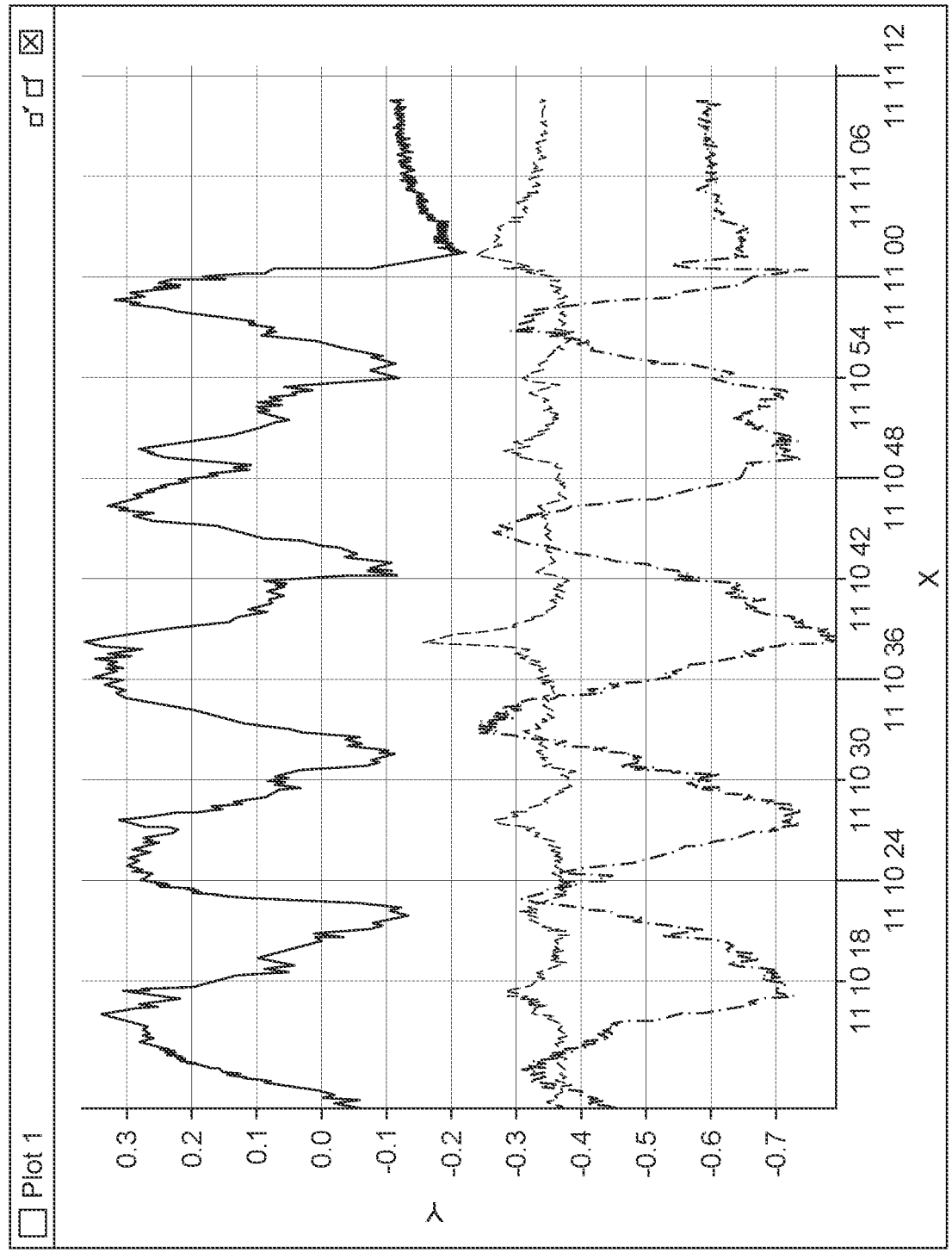
FIG. 6(b) is a graph of the magnetometer data from the horse vest of FIG. 6(a) demonstrating the continuous movement of the horse.

FIG. 6(a) shows a schematic view from above of a horse 5 in its stall or stable 28 wearing the horse vest 1 of FIG. 4 fitted with the motion sensor 3b in the form of a magnetometer 3b with the horse 5 exhibiting box walking behavior. Box walking can be indicative of stress or an underlying health/wellbeing problem in a horse 5. FIG. 6(b) shows a graph of the magnetometer data from the horse vest 1 of FIG. 6(a) and demonstrates that the continuous box walking motion of the horse was detected by the magnetometer 3b to alert a remote user monitoring the horse 5 that the horse may be in distress.

Figure 7A:
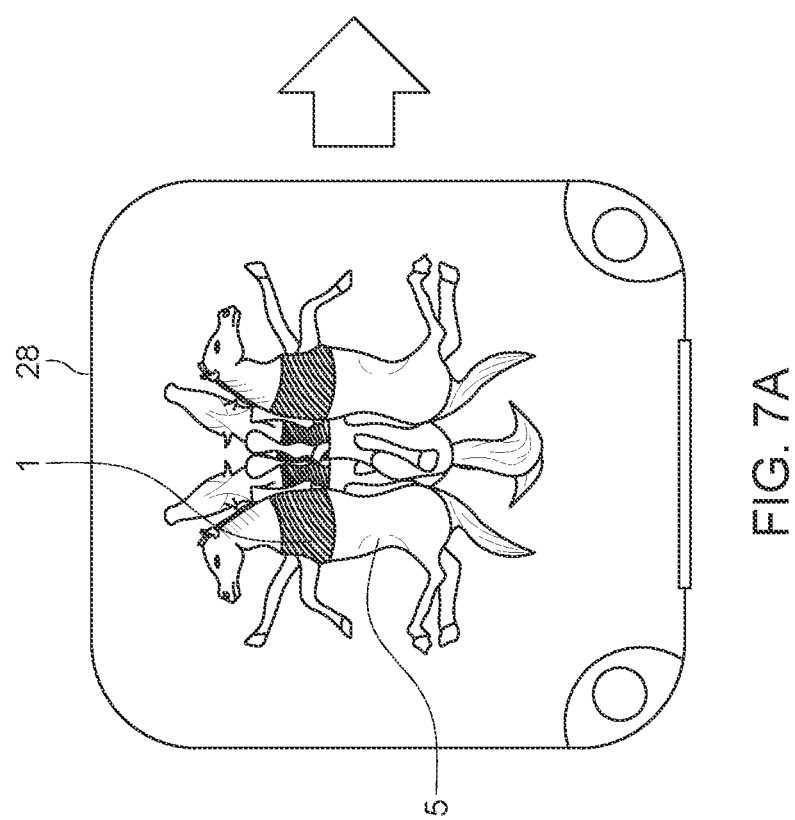
FIG. 7(a) is a schematic view from above of a horse in its stable wearing the horse vest of FIG. 4 fitted with a movement sensor in the form of an accelerometer with the horse exhibiting normal rolling behaviour.
Figure 7B:
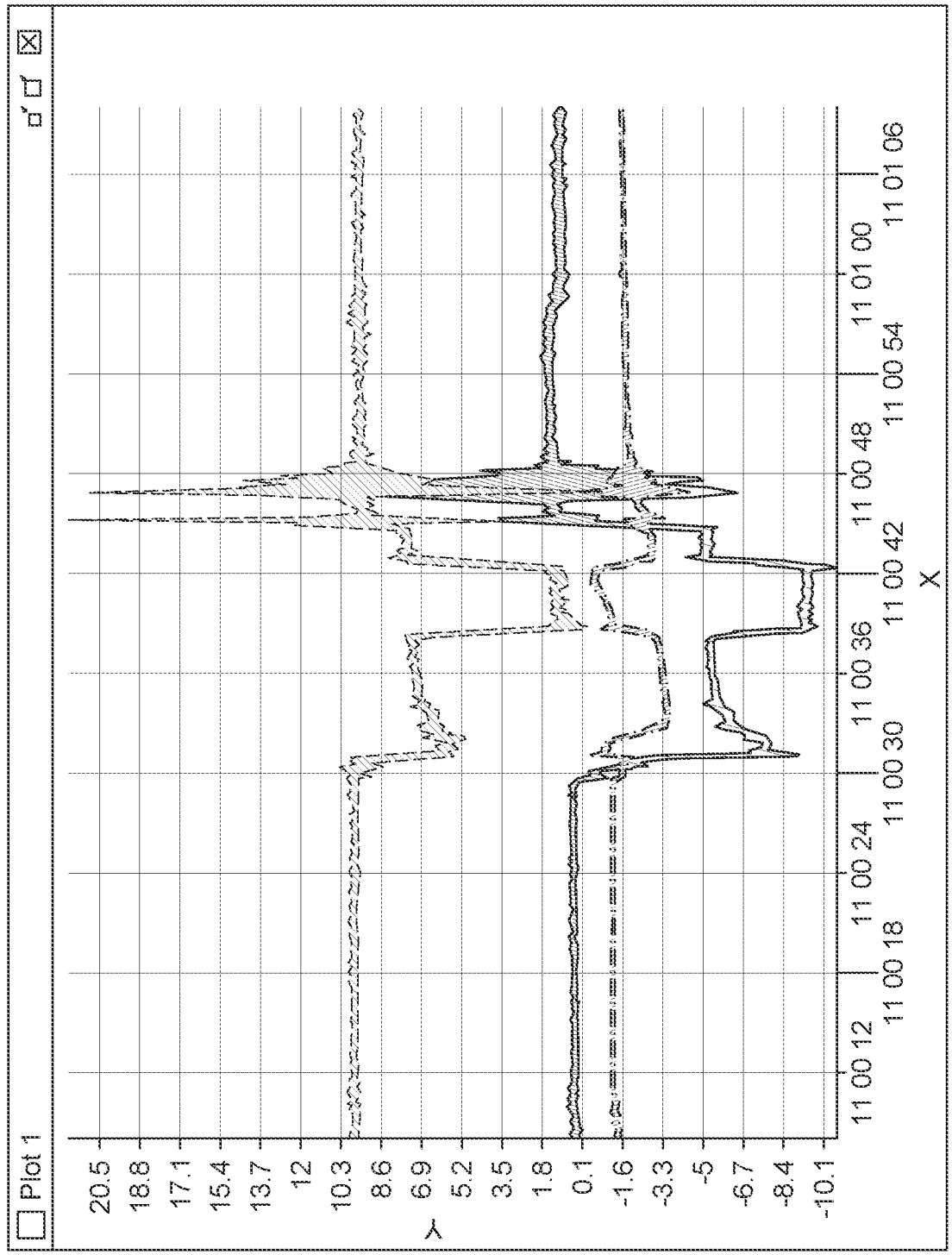
FIG. 7(b) is a graph of the accelerometer data from the horse vest of FIG. 7(a) demonstrating the normal rolling movement of the horse.

FIG. 7(a) shows a schematic view from above of a horse 5 in its stable 28 wearing the horse vest 1 of FIG. 4 fitted with a motion sensor 3b in the form of an accelerometer with the horse 5 exhibiting normal rolling behavior. FIG. 7(b) shows a graph of the accelerometer data from the horse vest 1 of FIG. 7(a) and demonstrates that the rolling movement of the horse was a normal event and that the horse 5 was otherwise stationary.

Figure 8A:
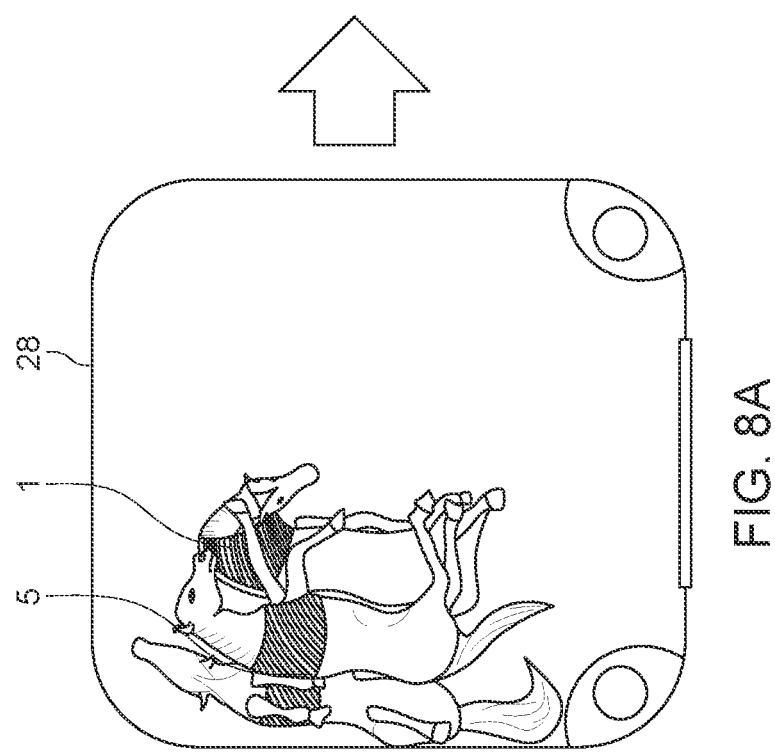
FIG. 8(a) is a schematic view from above of a horse in its stable wearing the horse vest of FIG. 4 fitted with a movement sensor in the form of a gyroscope with the horse experiencing an alarm event in the form of casting—e.g. the horse has lain down or rolled and positioned itself with its legs so close to the stall wall that the horse can neither get up nor reposition himself to roll the other way.
Figure 8B:
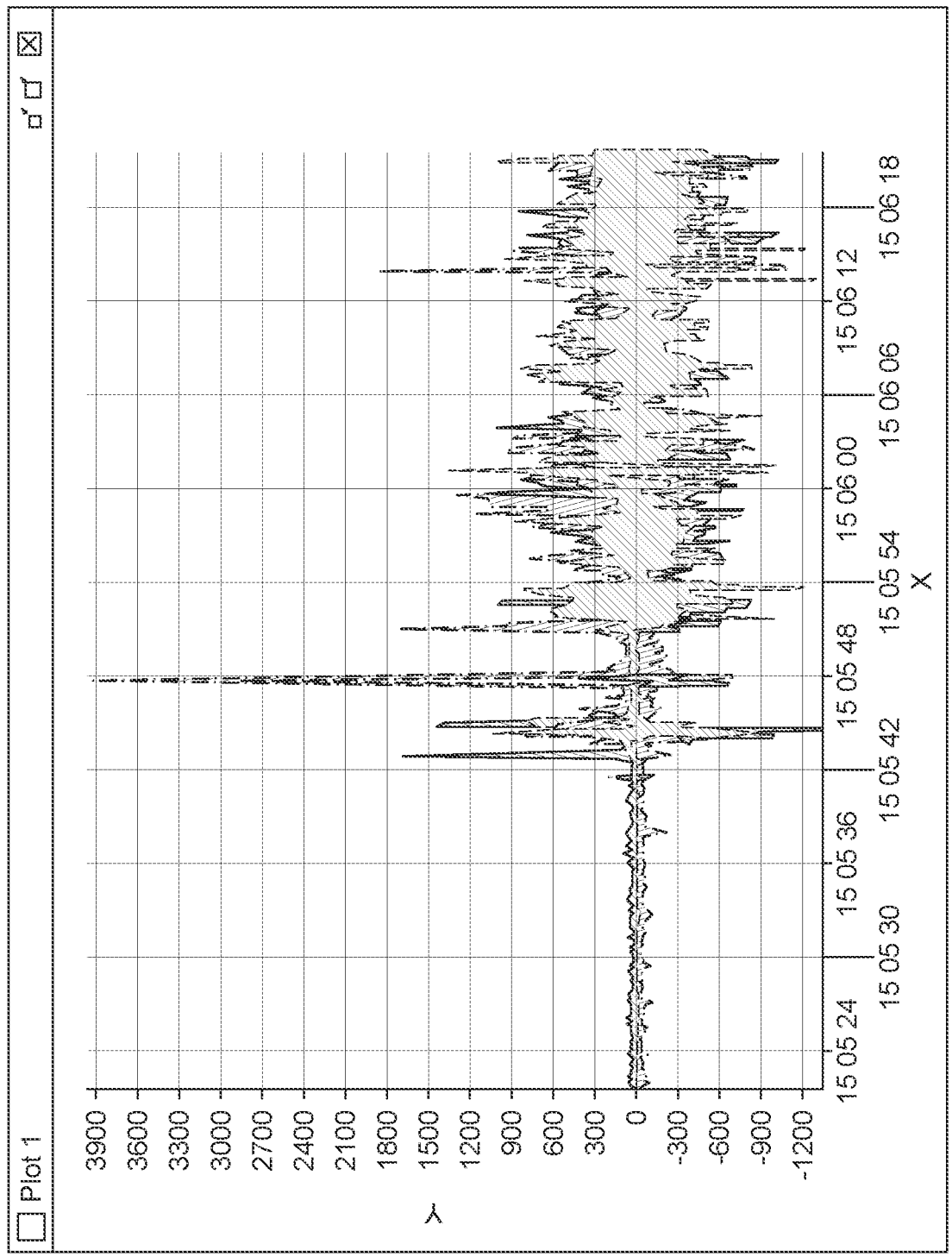
FIG. 8(b) is a graph of the gyroscope data from the horse vest of FIG. 8(a) demonstrating the casting alarm event for which an alert can be generated to come to the horse's aid.

FIG. 8(a) shows a schematic view from above of a horse 5 in its stable wearing the horse vest 1 of FIG. 4 fitted with a motion sensor 3b in the form of a gyroscope 3b with the horse experiencing a critical or alarm event in the form of casting—e.g. the horse has lain down or rolled and positioned itself with its legs so close to the stall 28 wall that the horse can neither get up nor reposition himself to roll the other way. FIG. 8(b) shows a graph of the gyroscope data from the horse vest of FIG. 8(a) demonstrating the casting alarm event in the otherwise stationary horse 5 for which a user alert was generated so that the user could come to the horse's aid.

Figure 9B:
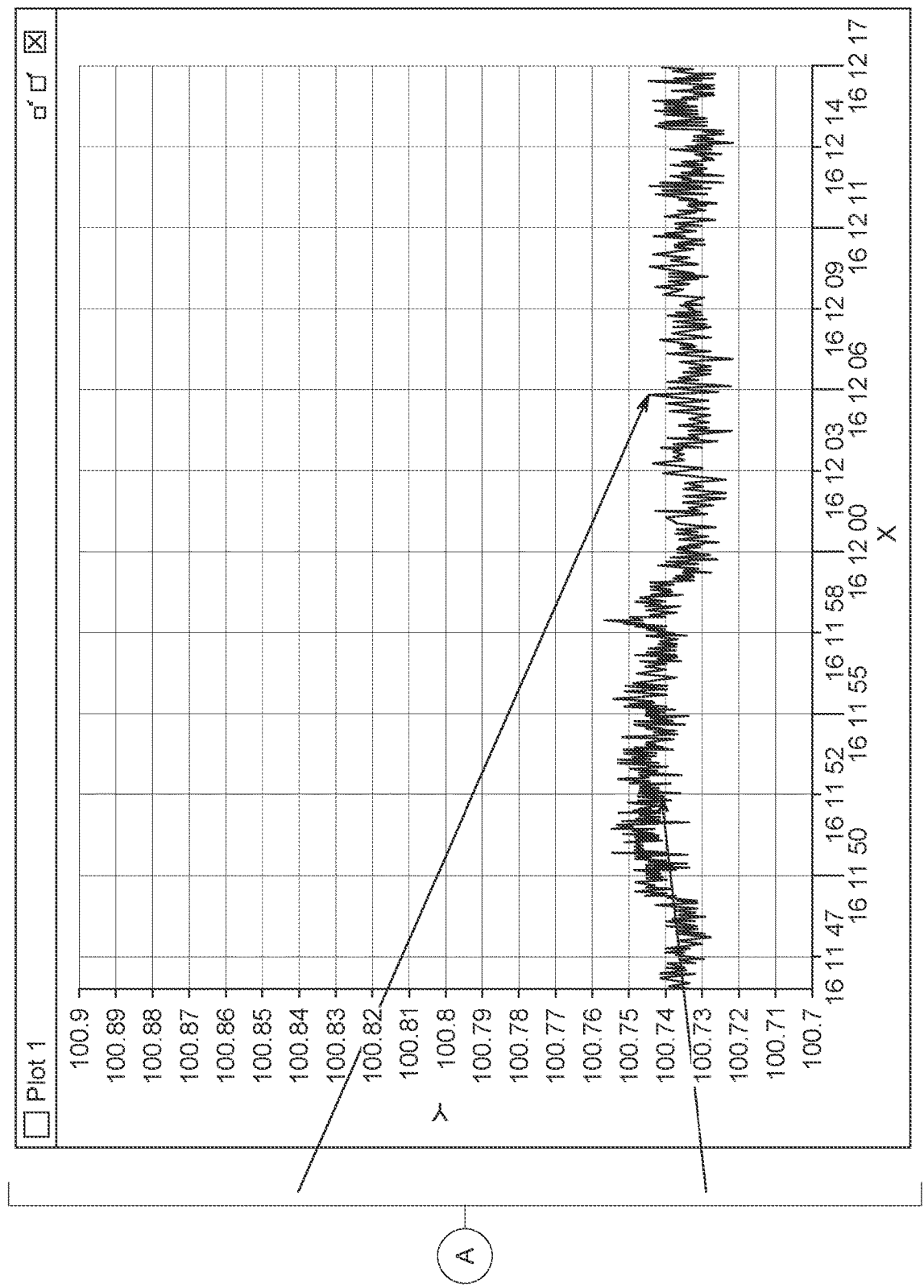
FIG. 9(b) is a graph of the barometric pressure sensor data from the horse vest of FIG. 9(a) demonstrating the lower pressure detected with the horse in the standing position and the higher pressure detected with the horse in the lying position.

FIG. 9(a) shows a schematic view from above of a horse 5 in its stable wearing the horse vest 1 of FIG. 4 fitted with a barometric pressure sensor 3 with the horse 5, firstly, in a standing position 29 and, secondly, in a lying position 30. FIG. 9(b) shows a graph of the barometric pressure sensor 3 data from the horse vest 1 demonstrating the lower pressure detected with the horse 5 in the standing position 29 and the higher pressure detected with the horse in the lying position 30. The barometric pressure data therefore served to monitor the standing/lying position of the horse to determine whether the horse was lying or standing excessively which could be indicative of an alarm event e.g. foaling or distress.

Figure 10B:
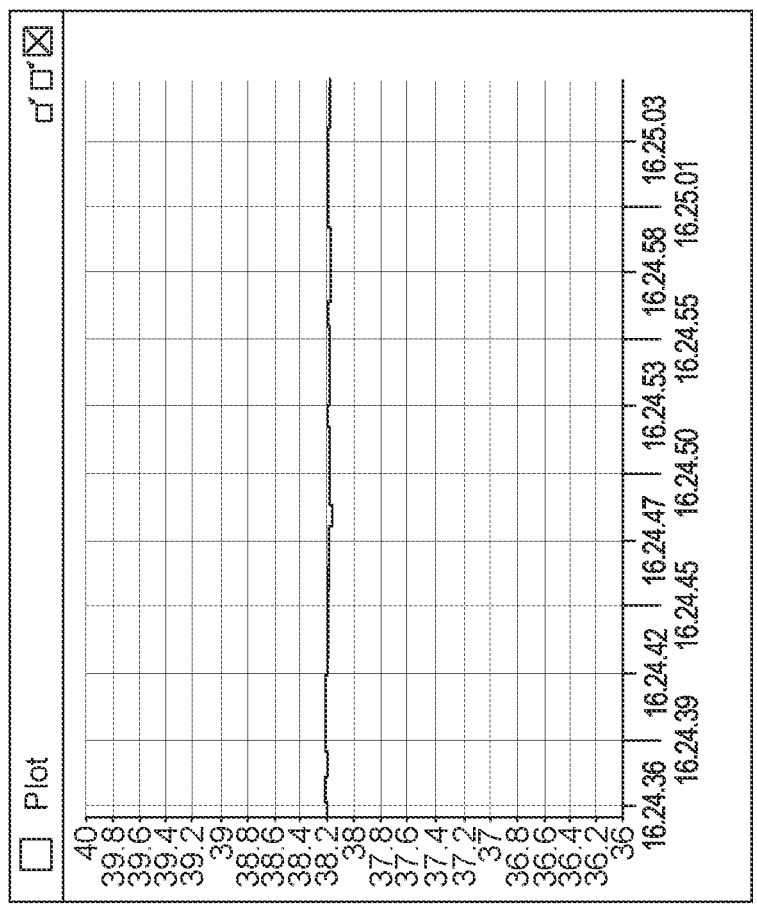
FIG. 10(b) is a graph of the temperature sensor data from the horse vest of FIG. 10a demonstrating that the horse's temperature is normal and constant.
Figure 10A:
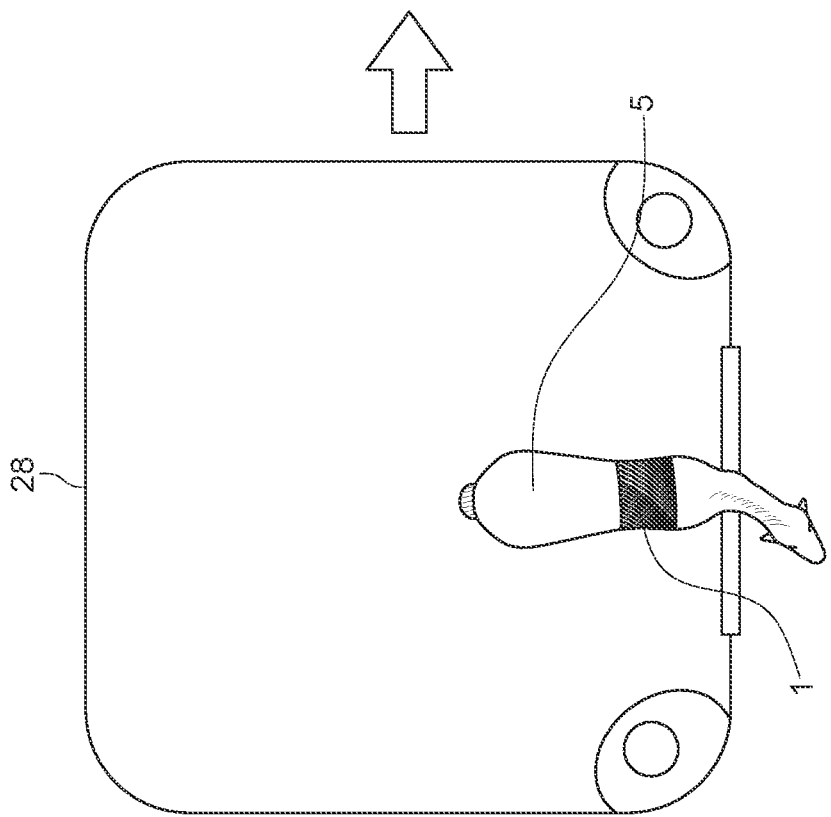
FIG. 10(a) is a schematic view from above of a horse in its stable wearing the horse vest of FIG. 4 fitted with a temperature sensor.

FIG. 10(a) shows a schematic view from above of a horse 5 in its stable 28 wearing the horse vest 1 of FIG. 4 fitted with a temperature sensor 3a and FIG. 10(b) shows a graph of the temperature sensor data from the horse vest 1 demonstrating that the horse's temperature remained normal and constant so that no alarm event arose.

FIG. 11 shows a combined graph and sequential CCTV images 31 of a mare 5 fitted with the smart vest 1 of FIG. 4 incorporating a motion sensor 3b in the form of an accelerometer 3b with the mare 5 in foal with the CCTV images 31 corroborating the accelerometer foaling data over a ten minute period. In particular, the sequential positional movements of the mare 5 immediately before and during foaling is recorded and demonstrated by the graph and the CCTV images 31.

Figure 12:
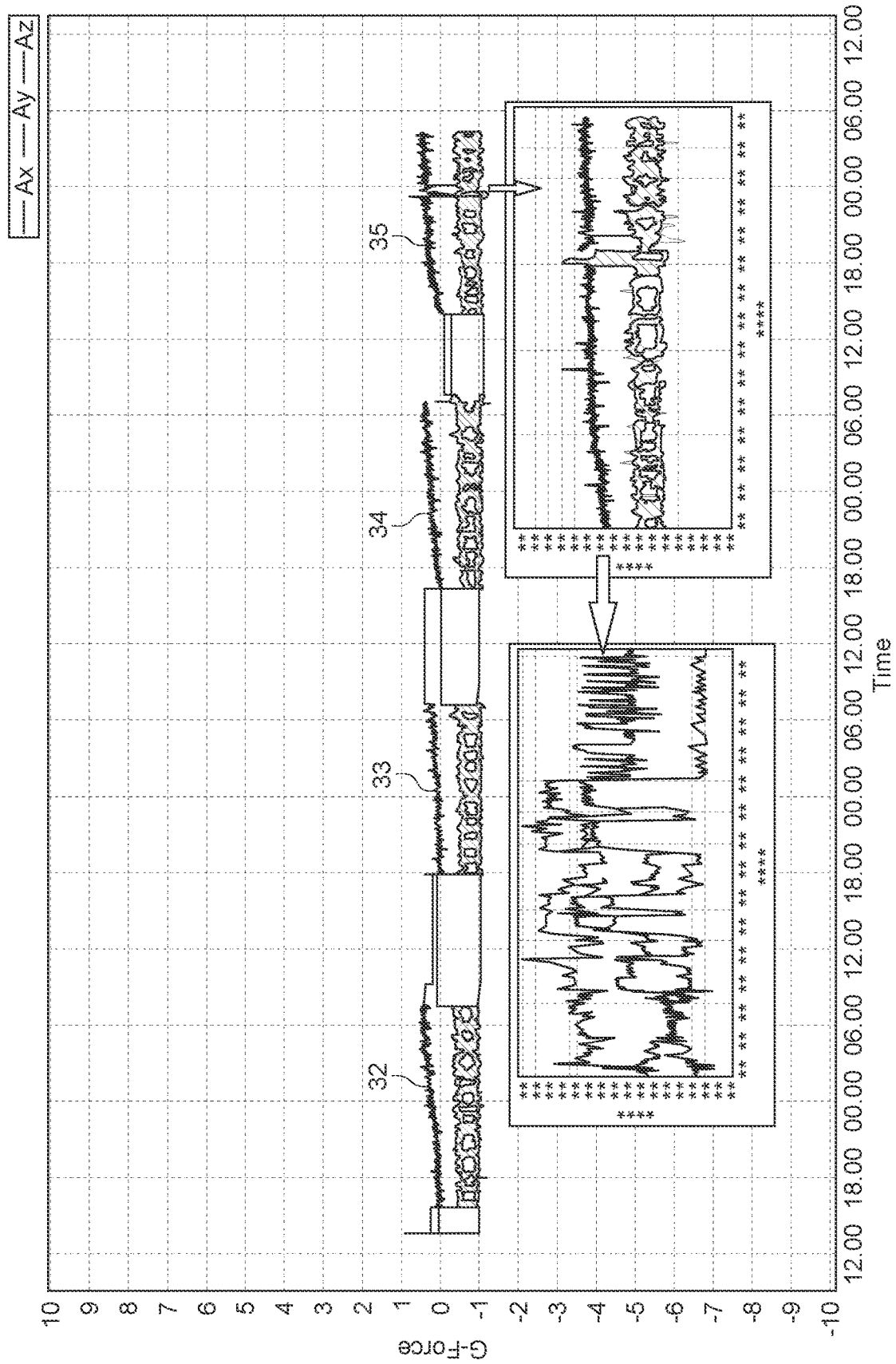
FIG. 12 is a graph of the accelerometer data from the horse vest and mare of FIG. 11 over a four day period demonstrating the foaling event on the fourth day together with enlarged images of the foaling event similar to that show in FIG. 11.
Figure 13:
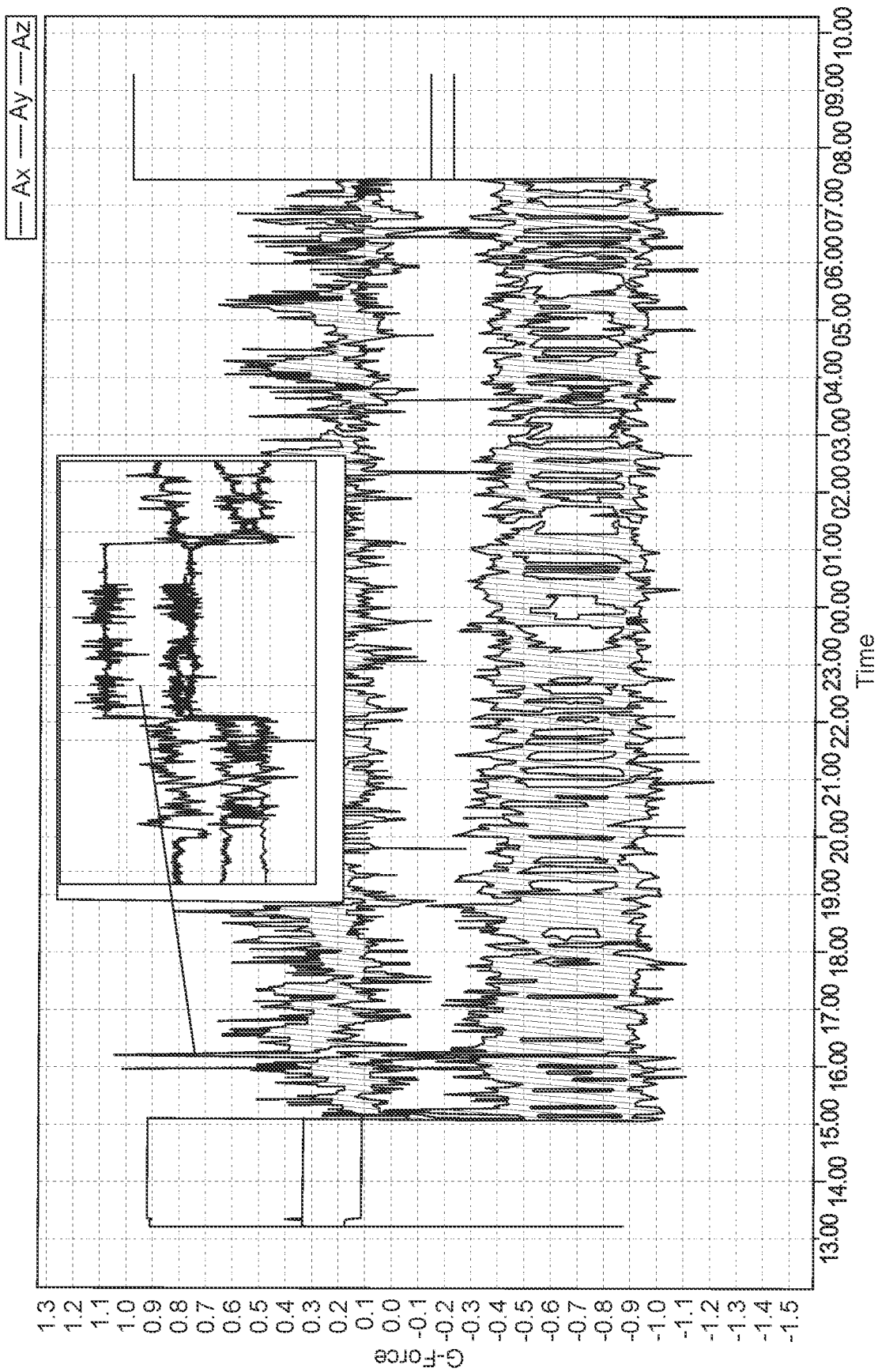
FIG. 13 is a graph of the accelerometer data from the horse vest and mare of FIG. 11 over a single day demonstrating the foaling event.

FIG. 12 shows a graph of the accelerometer data from the horse vest 1 and mare 5 of FIG. 11 over a sequential four day period 32, 33, 34, 35 respectively demonstrating the observable foaling event on the fourth day 35 in comparison with the previous three days 32, 33, 34. Similarly, FIG. 13 shows a graph of the accelerometer data from the horse vest 1 and mare 5 of FIG. 11 over a single day demonstrating the foaling event.

Figure 14:
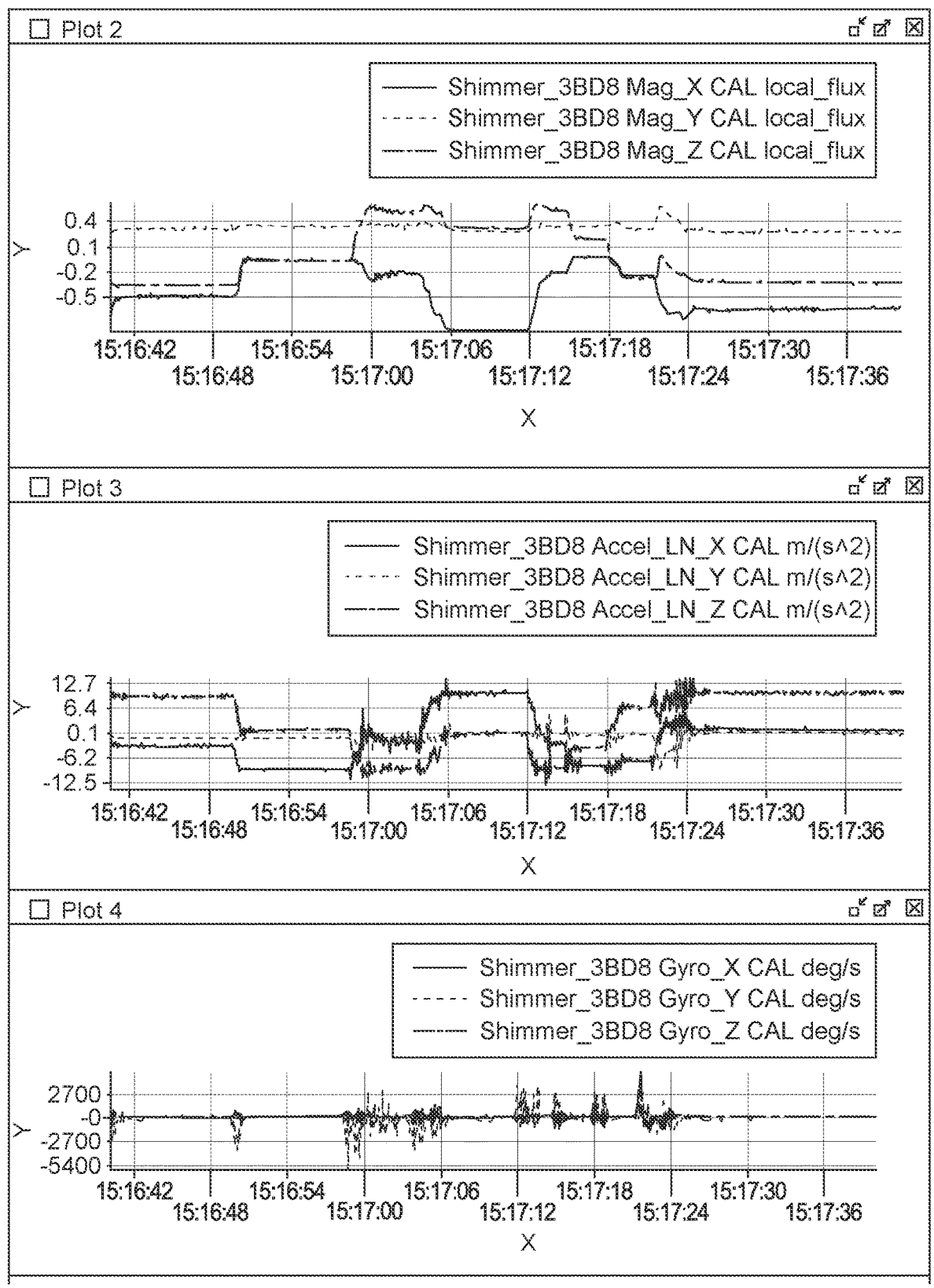
FIG. 14 is a multiple graph of the data from three movement sensors fitted in the horse vest of FIG. 4, namely a magnetometer, an accelerometer and a gyroscope to determine possible alarm events such as casting and foaling.

FIG. 14 shows a multiple graph of the data from three movement sensors 3b fitted in the horse vest 1 of FIG. 4, namely a magnetometer 3b, an accelerometer 3b and a gyroscope 3b to determine possible alarm events such as casting and foaling as described above.

Accordingly, as shown in the drawings, it was possible to easily determine each subject's movement/orientation/position from the motion sensors 3b of the smart vest 1 recording at 10 Hz while the stress levels of the subject's was also determined based on this movement i.e. unusual/uncharacteristic movement based on each subject's normal movement patterns in conjunction with increased skin temperature and increased sweat levels.

It was found that a combination of just three sensor metrics i.e. motion, temperature and respiration/skin impedance was sufficient to provide a highly complex and robust subject wellbeing evaluation. However, as indicated above, while these three sensor metrics alone prove very effective, other sensor metrics such as pressure sensors, respiration sensors, sound sensors, security sensors and cameras can be included in the smart garment of the invention as required.

Moreover, based on the collated data generated, it was possible to determine and set preset parameter safety thresholds which if breeched generated an alert as described in FIG. 5.

The above trial was repeated with seven racehorses under similar conditions to those described above and the result achieved demonstrated that the blanket 1 of the invention was highly effective at safely monitoring the safety and wellbeing of the racehorses.

The invention claimed is:

1. A horse monitoring garment for monitoring health and wellbeing of a horse, the garment comprising:
   a back portion arranged to lie on the horse's back;
   a side portion depending from the back portion and supporting a heart monitor sensor;
   a chest portion arranged to lie against the horse's chest, the chest portion supporting a monitor communicable with a user for communicating data from the garment to the user; and
   a sensor zone extending from either side of the monitor from the chest portion toward the back portion and containing sensors connected to the monitor, those sensors also comprising a heart monitor sensor.

2. A horse monitoring garment as claimed in claim 1, wherein the sensors contained in the sensor zone further comprise at least one moisture sensor.

3. A horse monitoring garment as claimed in claim 2, wherein the at least one moisture sensor comprises a galvanic skin response electrode.

4. A horse monitoring garment as claimed in claim 1, wherein the chest portion further supports at least one movement sensor.

5. A horse monitoring garment as claimed in claim 4, wherein the at least one movement sensor comprises an inertia sensor.

6. A horse monitoring garment as claimed in claim 1, wherein the chest portion further supports at least one temperature sensor.

7. A horse monitoring garment as claimed in claim 6, wherein the at least one temperature sensor comprises an IR and/or thermocouple temperature sensor.

8. A horse monitoring garment as claimed in claim 1 and being suitable for twenty four hour monitoring of the horse in a stall or a stable.

9. A horse monitoring garment as claimed in claim 1, further comprising at least one sensor selected from the group consisting of pressure sensors, respiration sensors, sound sensors, security sensors, global positioning system sensors and cameras.

10. A system for monitoring a horse, the system comprising a horse monitoring garment as claimed in claim 1 and an external communications hub communicable with the monitor and with the user.

11. A system as claimed in claim 10 and further comprising an analytics module communicable with the communications hub for analysing data from the sensors.

12. A system as claimed in claim 10 and further comprising an alert/flag system for generating alerts/flags for the user.

13. A system as claimed in claim 10 and further comprising at least one environmental sensor for detecting ambient conditions adjacent the garment.

14. A system as claimed in claim 13, wherein the at least one environmental sensor is located at the communications hub.

15. A system as claimed in claim 13 wherein the at least one environmental sensor is selected from the group consisting of air quality sensors, ambient light sensors, thermometers and cameras.

16. A horse garment as claimed in claim 1 wherein the back portion, side portion and chest portion position the at least one sensor close to a desired horse anatomical feature.

17. A horse garment for twenty four hour monitoring of a health and wellbeing of the horse in a stall or a stable, the horse garment comprising:
   a back portion;
   a side portion depending from the back portion;
   a chest portion;
   at least one sensor on the garment communicable with a user,
   wherein the back portion, the side portion, and the chest portion are configured so that the horse garment is mountable on a horse trunk or a horse torso to locate the at least one sensor at the horse's trunk or the horse's torso, and
   wherein the at least one sensor comprises a motion sensor positioned at the chest portion of the garment.

18. A horse garment as claimed in claim 1, wherein the horse garment is adapted to conform in shape and configuration to the anatomy of a horse.

* * * * *